(12) United States Patent
Bombulie et al.

(10) Patent No.: US 8,800,394 B2
(45) Date of Patent: Aug. 12, 2014

(54) TRANSPORTABLE LIQUID PHASE LNG SAMPLE APPARATUS AND METHOD

(75) Inventors: Michael A. Bombulie, Conroe, TX (US); Tracy D. Peebles, Houston, TX (US)

(73) Assignee: Welker, Inc., Sugar Land, TX (US)

( * ) Notice: Subject to any disclaimer, the term of this patent is extended or adjusted under 35 U.S.C. 154(b) by 664 days.

(21) Appl. No.: 13/090,236

(22) Filed: Apr. 19, 2011

(65) Prior Publication Data

US 2011/0192237 A1 Aug. 11, 2011

Related U.S. Application Data

(63) Continuation-in-part of application No. 12/234,602, filed on Sep. 19, 2008, now Pat. No. 8,210,058.

(51) Int. Cl.
*G01N 1/20* (2006.01)
*G01N 1/10* (2006.01)
*G01N 1/42* (2006.01)

(52) U.S. Cl.
CPC ............... *G01N 1/2042* (2013.01); *G01N 1/10* (2013.01); *G01N 1/42* (2013.01); *G01N 2001/105* (2013.01)
USPC ......................... 73/864.62; 73/863.11; 374/36

(58) Field of Classification Search
CPC ......... G01N 1/10; G01N 1/2042; G01N 1/42; G01N 2001/105; G01N 2001/2035
USPC ........ 73/863.11, 863.71, 864.62; 374/36, 157
See application file for complete search history.

(56) References Cited

U.S. PATENT DOCUMENTS 2,791,698 A    5/1957   Dyroff et al.
3,487,692 A    1/1970   Cook, Jr.
3,789,670 A *  2/1974   Rosenwald ................. 73/864.62

(Continued)

FOREIGN PATENT DOCUMENTS

| FR | 2911795 A1 * | 8/2008 | ............. B01D 21/02 |
| FR | 2921489 A1 * | 3/2009 | ............... G01N 1/10 |
| JP | 08210952 A * | 8/1996 | ............... G01N 1/00 |
| WO | WO 2006091543 A2 * | 8/2006 | ....... G01N 2001/105 |

OTHER PUBLICATIONS

Refrigerated Light Hydrocarbon fluids—Sampling of Liquefied Natural Gas—Continuous and Intermittent Methods, International Standard 8943, Second Edition, Mar. 1, 2007, pp. i-vi and 1-20.

(Continued)

*Primary Examiner* — Thomas P Noland
(74) *Attorney, Agent, or Firm* — Husch Blackwell LLP

(57) ABSTRACT

A transportable Sample Apparatus includes a vacuum flask (Dewar flask) and integral sample container. The Sample Apparatus may be used to capture a liquid phase LNG sample at a custody transfer point and to transport the sample to a laboratory for analysis. Vaporization of the liquid phase sample may take place at a variety of different locations. For example, vaporization may begin and/or be completed during transport from the collection point to the laboratory. In another example, vaporization may begin and be completed in the laboratory. In yet another example vaporization may begin during transport and be completed at the laboratory. The gas phase sample is typically analyzed by a gas chromatograph for Btu content, among other things. Prior to capture of the sample, the Sample Apparatus goes through a pre-cool cycle to chill a sample end cap and other components to a temperature compatible with capture of a cryogenic liquid sample which is about −250° F.

10 Claims, 6 Drawing Sheets

(56) References Cited

U.S. PATENT DOCUMENTS

| | | | |
|---|---|---|---|
| 3,793,886 A * | 2/1974 | Rosenwald | 73/864.62 |
| 3,793,888 A * | 2/1974 | Rosenwald | 73/864.62 |
| 4,457,171 A | 7/1984 | Gebauer | |
| 4,628,750 A | 12/1986 | Welker | |
| 4,882,939 A * | 11/1989 | Welker | 73/864.62 X |
| 4,922,764 A | 5/1990 | Welker | |
| 5,337,822 A | 8/1994 | Massie et al. | |
| 5,526,680 A | 6/1996 | McLaughlin | |
| 6,116,098 A | 9/2000 | Lubek et al. | |
| 6,422,737 B1 | 7/2002 | Welker | |
| 7,481,125 B2 | 1/2009 | Mayeaux | |
| 7,555,965 B1 * | 7/2009 | Mayeaux | 73/864.62 |
| 2008/0041163 A1 | 2/2008 | Tohidi et al. | |

OTHER PUBLICATIONS

Natural Gas—Sampling Guidelines, International Standard 10715, First Edition, Jun. 1, 2007, pp. i-iv and 1-40.

Obtaining Natural Gas Samples for Analysis by Gas Chromatography, Gas Processors Association, GPA Standard 2166-05, Revised 2005, Tulsa, Oklahoma, www.gasprocessors.com, pp. 1-42.

Manual of Petroleum Measurement Standards, Chapter 14—Natural Gas Fluids Measurement, Section 1—Collecting and Handling of Natural Gas Samples for Custody Transfer, Sixth Edition, Feb. 2006 , cover page, forward page, 3 pages table of Contents, pp. 1-61 in chapter.

* cited by examiner

TRANSPORTABLE LIQUID PHASE LNG SAMPLE APPARATUS AND METHOD

CROSS-REFERENCE TO RELATED APPLICATION

This application is a continuation-in-part of prior U.S. application Ser. No. 12/234,602 entitled "LNG Sampling Cylinder and Method" filed on Sep. 19, 2008 which application is hereby incorporated by reference to the extent permitted by law.

BACKGROUND OF THE INVENTION

Some countries, like Japan, have little or no domestic supply of natural gas. To meet this demand, natural gas produced in Indonesia and/or the Middle East is liquefied and shipped to market in the liquid phase. Upon arrival in Japan, the LNG is offloaded from ships to land based LNG receiving terminals where it is stored in surface tanks in the liquid phase. When users need natural gas, the LNG is vaporized at the receiving terminal and pumped into pipelines for transmission to buyers and sellers. These pipelines vary in length. For example, some electrical generating plants in Japan are built proximate the LNG receiving terminals. Other areas of the world also import LNG, for example, Europe imports LNG from North Africa and elsewhere. The United States also has several LNG receiving terminals that were developed prior to improvements in production of shale gas.

As the LNG is bought and sold, the product needs to be analyzed at each custody transfer point, typically by a gas chromatograph (GC) to determine the Btu content of the product. GC's do not analyze liquids. Price is generally based on the Btu content. Capture of a representative sample and proper analysis is important to buyers and sellers because millions of dollars are exchanged at each custody transfer point.

One early attempt to develop a liquid phase LNG sample collection device is disclosed in U.S. Pat. No. 3,487,692 filed on May 24, 1968 entitled "Method and Apparatus for Sampling Refrigerated Volatile Liquids". During the 1960's and early 1970's, no single product or procedure received universal approval by both buyers and sellers.

To achieve some standardization in the industry, the International Organization for Standardization ("ISO") approved three systems for sampling LNG based on a gas phase sample. Standard No. 8943 dated 2007, Mar. 1 has enjoyed wide acceptance on a worldwide level by both buyers and sellers. ISO Standard No. 8943 has been the worldwide benchmark for LNG sampling since it was adopted in 1977.

FIG. 1 of ISO Standard 8943 is a diagram for a first LNG sampling system entitled "Example of continuous sampling for a water-seal-type gas sample holder with a compressor." This procedure vaporizes the LNG prior to capture in a sample cylinder. This sample cylinder with a gas phase sample is then taken to a laboratory for analysis.

FIG. 2 of ISO 8943 is a diagram for a second LNG sampling system entitled "Example of continuous sampling for a waterless-type gas sample holder". This procedure also vaporizes the LNG prior to capture in a sample cylinder. This sample cylinder with a gas phase sample is then taken to a laboratory for analysis.

FIG. 3 of ISO 8943 is a diagram for a third LNG sampling system entitled "Example of intermittent sampling for CP/FP sample container." The CP/FP designation stands for a constant pressure floating piston sample container made by Welker, Inc., assignee of the present application. Like the sample cylinders in FIGS. 1, 2, the CP/FP cylinder also stores a gas phase sample which is then taken to a laboratory for analysis. The Assignee of the present application currently produces sample collection cylinders used in all three systems discussed in this ISO Standard. The present invention is an improvement on the systems described in this ISO Standard.

Unlike the aforementioned prior art which captures the sample in the gas phase, the present invention captures the sample in the liquid phase in a transportable liquid phase LNG sample apparatus (Sample Apparatus). This Sample Apparatus is then taken to a laboratory.

Vaporization of the liquid phase sample may take place at a variety of different locations. For example, vaporization may begin and end during transport from the collection point to the laboratory. In another example, vaporization may begin and end in the laboratory. In yet another example, vaporization may begin during transport and be completed at the laboratory. The liquid phase sample must be allowed to vaporize to the gas phase before analysis because a GC can only analyze gases, as is well known to those skilled in the art. The present invention eliminates substantially all of the equipment in FIGS. 1, 2 and 3 of this ISO Standard, saving money and reducing the chance of leaks and contamination of the sample. Applicant believes that the present sampling apparatus allows both buyers and sellers to capture and transport a more representative sample than any of the prior art listed above.

U.S. patent application Ser. No. 12/234,602 entitled "LNG Sampling Cylinder and Method" filed by the assignee of the present application was an attempt to develop a sample apparatus that could capture a sample in the liquid phase for subsequent delivery to the lab. Unfortunately, the cooling cycle, which must be completed prior to capturing a sample, of this apparatus was lengthy, which delayed field operations. The present invention reduces the length of the cooling cycle and elongates the amount of time available to capture a liquid phase sample.

SUMMARY OF THE INVENTION

Unlike all the approved systems in the aforementioned ISO Standard, the present invention captured a liquid phase sample of LNG rather than a gas phase sample of LNG. Because LNG is so cold, (About −250° F.) it is necessary to pre-cool the present Sample Apparatus prior to capture of the liquid phase LNG sample. Pre-cooling is accomplished by transferring a cryogenic liquid, e.g. liquid Nitrogen, into an inner cryogenic vessel that is permanently attached to the Sample Apparatus. A vacuum flask and a LNG sample container form a one piece design that may henceforth sometime be referred to as an integral Sample Apparatus.

The pre-cool cycle of the present invention is quick and gives technicians plenty of time to thereafter capture the sample of liquid phase LNG. The present sample apparatus weighs less than about 45 pounds filled with liquid phase Nitrogen and with liquid phase LNG so it is easy to transport.

Unlike all the approved systems in the current ISO Standard, there is no need for costly vaporization systems at the ship, pipeline or other custody transfer points. The present Sample Apparatus captures the sample at the ship or pipeline in the liquid phase.

DETAILED DESCRIPTION OF THE INVENTION

Figure 1:
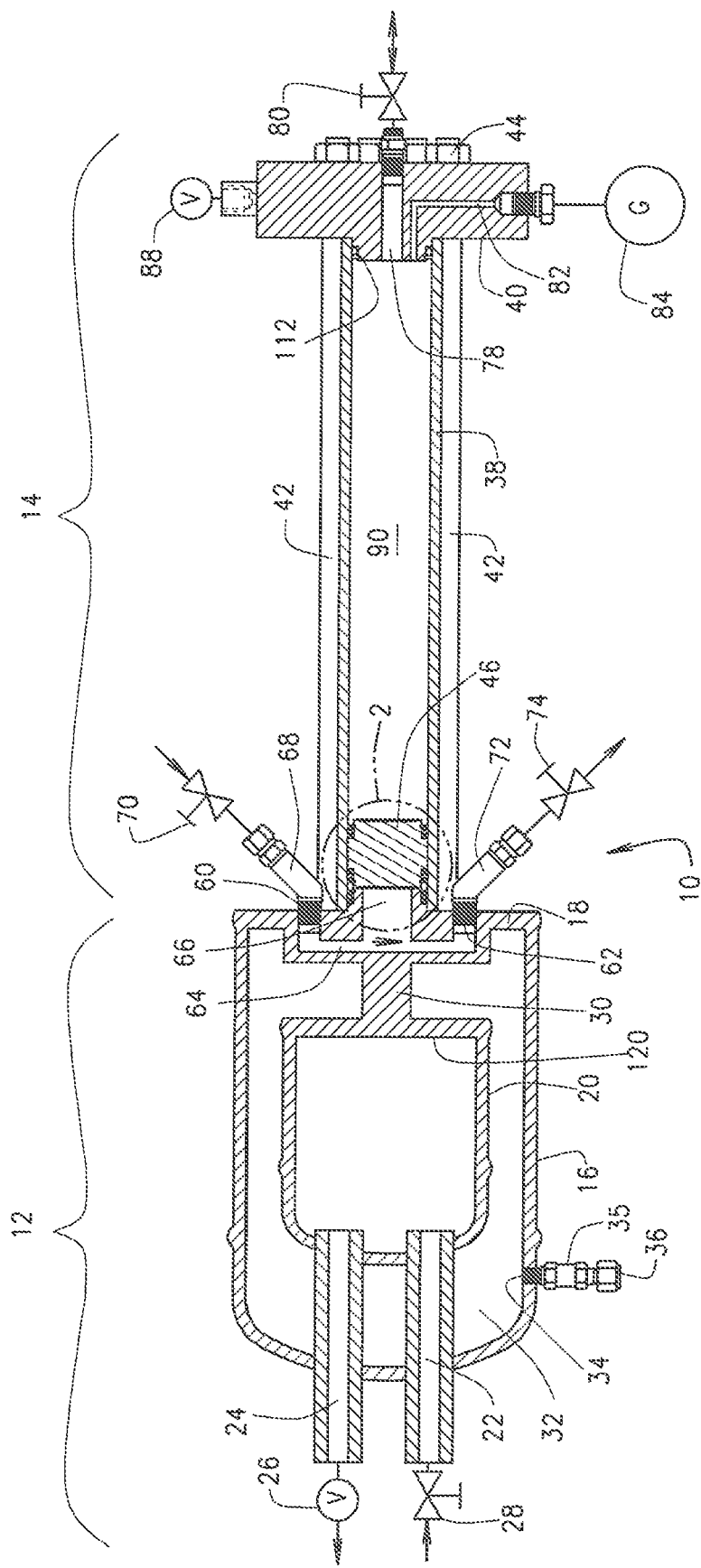
FIG. 1 is a section view of the Sample Apparatus including the vacuum flask and sample container.

FIG. 1 is a section view of the Sample Apparatus 10, the vacuum flask identified by the bracket 12 and the sample container identified by the bracket 14. The vacuum flask is formed by an outer shell 16 connected to the sample end cap 18. An inner cryogenic vessel 20 includes a base 120; the inner cryogenic vessel 20 is surrounded by the outer shell of the vacuum flask. The inner cryogenic vessel 20 is filled with a cryogenic liquid to pre-cool the Sample Apparatus prior to capture of a liquid phase sample of LNG in the sample collection chamber 66, discussed in greater detail below.

A vacuum chamber 32 is defined by the outside surface of the cryogenic vessel, the sample end cap and the inside surface of the outer shell. A vacuum port 34 passes through the outer shell and is connected to a one way check valve 35 to maintain the vacuum in the vacuum chamber 32. A tube connection 36 is in fluid communication with the one-way check valve to facilitate connection to a vacuum pump not shown. The vacuum pump is connected to the tube connection to pull a vacuum in the vacuum chamber so as to act as an insulation barrier for the cryogenic liquid in the cryogenic vessel 20.

A fill port 22 passes through the outer shell and is in fluid communication with the cryogenic vessel. A vent port 24 is in fluid communication with the cryogenic vessel and passes through the outer shell to atmosphere. A burping relief valve 26 is positioned in the vent port and is set to a preselected level. When the burping relief valve is in the open position, gas may pass through the vent port and the burping relief valve as it vaporizes in the cryogenic vessel, thus preventing overpressure in the cryogenic vessel. This burping relief valve is typically in the closed position and set to a preselected point. When pressure in the cryogenic vessel reaches or exceeds the preselected point, the valve opens, relieving overpressure in the cryogenic vessel. The burping relief valve then resets to the normally closed position. A heat exchange element 30 is in contact with a portion of the cryogenic vessel and a portion of the sample end cap to facilitate chilling of the sample end cap 18, and other components of the sample container 14. The heat exchange element 30 is a means for transferring heat from the sample end cap 18 to the cryogenic vessel to pre-cool the end cap and the LNG sample collection chamber. In one embodiment, the cross-sectional area of the heat exchange element 30 may be about 0.7854 square inches. Other cross-sectional areas may be used depending on the size of the particular embodiment. Alternative embodiments, discussed below, show alternative designs for the means for transferring heat. Other alternative embodiment shown in FIG. 8 uses a unitary design, discussed in greater detail below as a means for transferring heat. Prior to capture of the liquid phase sample of LNG, the Sample Apparatus must be pre-cooled by transferring a cryogenic fluid, e.g. liquid Nitrogen, into the cryogenic vessel. When full, a shut off valve 28 or plug is placed in the cryogenic fill port 22 and the burping relief valve 26 is threaded in the vent port 24.

A hollow cylinder 38 is captured between the sample end cap 18 and the pre-charge end cap 40. The pre-charge end cap is perforated by a circle of bolt holes, not shown, around the outside circumference of the hollow cylinder. A plurality of bolts 42 pass through the bolt holes, not shown, in the pre-charge end cap and threadably engage the sample end cap. Each bolt threadably receives a nut 44 to capture the hollow cylinder between the sample end cap and the pre-charge end cap. As shown in FIG. 1, the piston 46 abuts the sample end cap and helps to define the sample collection chamber 66. The inside surface of the hollow cylinder 38 is honed and polished to facilitate sealing engagement between a) the piston and the hollow cylinder and b) the end caps and the hollow cylinder. The piston is free to move to and fro in the hollow cylinder based on pressure differentials acting on the piston.

The sample end cap 18 defines a sample inlet port 60, a sample outlet port 62, and a passageway 64 in fluid communication between the inlet port and the outlet port. A sample collection chamber 66 is defined by the sample end cap and a portion of the piston. The sample collection chamber is in fluid communication with the sample inlet port, the sample outlet port, and the passageway. A conduit 68 connects the sample inlet port to a sample inlet valve 70. A conduit 72 connects the sample outlet port to a sample outlet valve 74. When the sample inlet valve and the sample outlet valve are open, fluid circulates through the sample inlet valve 70, the conduit 68, the passageway 64, the sample collection chamber 66, the sample outlet port 62, the conduit 72, and sample outlet valve 74 to a collection apparatus not shown. A temperature gauge 132 connects to the sample end cap, as better seen in FIG. 3.

A pre-charge port 78 is formed in the pre-charge end cap 40 and connects to a shut off valve 80. An optional pressure gauge port 82 is formed in the pre-charge end cap allowing fluid communication with the pre-charge chamber 90. An optional pressure gauge 84 threadably engages the pressure gauge port 82. A relief valve port, not shown, is formed in the pre-charge end cap allowing fluid communication between the pre-charge chamber 90 and atmosphere. A frangible bursting disc relief valve 88 is in fluid communication with the pre-charge chamber 90 to prevent overpressure of the pre-charge chamber as the LNG sample vaporizes.

There are two "make-ready" activities prior to taking the present Sample Apparatus into the field for collecting a liquid phase LNG sample. First, it is necessary to fill the pre-charge chamber 90 with a pre-charge fluid, e.g. gas phase Nitrogen. In order to fill the pre-charge chamber with pre-charge fluid, the technician opens the shut off valve 80 and the outlet valve 74. A pressurized fluid is pumped through the shut off valve 80 and the port 78 in the pre-charge end cap 40 thus moving the piston into contact with the sample end cap 18 as shown in FIG. 1. The shut off valve 80 is closed thus capturing fluid in the pre-charge chamber 90 at a preselected pressure. The outlet valve 74 is also closed. Second, a vacuum is pulled in the vacuum chamber 32 and the vacuum chamber is sealed against atmosphere. The present Sample Apparatus is then ready to be taken into the field.

In the field, the Sample Apparatus must first be pre-cooled before taking a sample of LNG. To pre-cool the Sample Apparatus, the valve 26 must be removed. A cryogenic fluid is transferred through inlet valve 28, through fill port 22 into the cryogenic vessel 20. Then, inlet valve 28 is closed and valve 26 is replaced, sealing the cryogenic fluid into the cryogenic vessel 20. A complete example is given below explaining how to obtain the liquid phase sample of LNG in the field.

Figure 2:
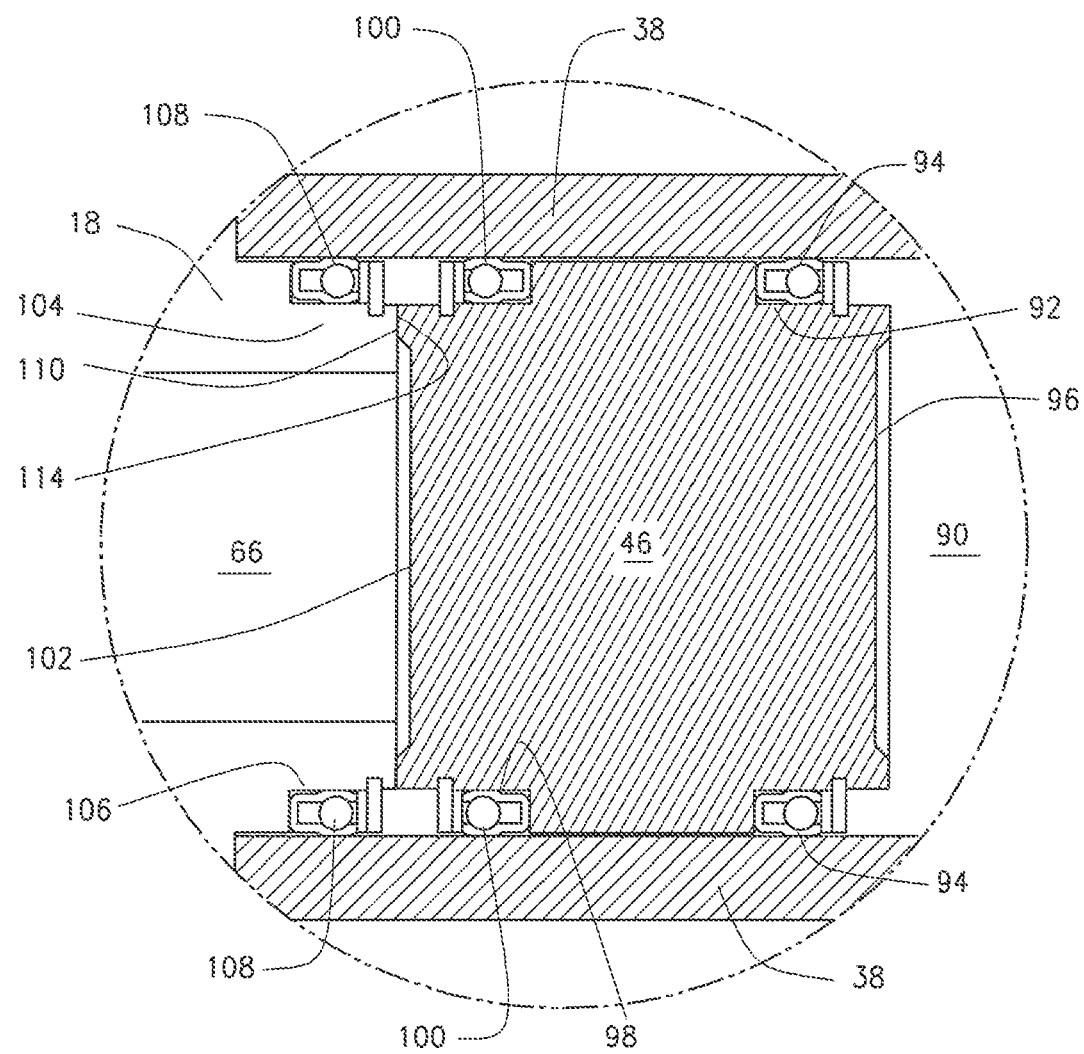
FIG. 2 is an enlarged section view of the piston that slides to and fro in the LNG sample container as circumscribed by circle 2 in the preceding figure.

FIG. 2 is an enlarged cross-section of the piston 46 and a portion of the hollow cylinder 38. In this view, the piston 46 is touching the sample end cap 18 as shown in FIG. 1. A channel 92 is formed in the outer circumference of the piston and is sized and arranged to receive a seal assembly 94. A slight indention is formed in the pre-charge face 96 of the piston 46. On the opposite side of the piston, another channel 98 is formed in the outer circumference of the piston and is sized and arranged to receive a seal assembly 100 which also seals against the hollow cylinder in a similar fashion as seal assembly 94. A slight indention is formed in the sample collection face 102 of the piston. The sample end cap 18 forms a neck 104 which includes a channel 106 which is sized and arranged to receive a seal assembly 108. The seal assembly 108 engages the hollow cylinder to form a seal between the sample end cap and the hollow cylinder, thus assisting in the formation of the sample collection chamber 66. Seal assembly 112, best seen in FIG. 1, on the pre-charge end cap 40 engages the hollow cylinder to form a seal between the pre-charge end cap and the hollow cylinder, thus assisting in the formation of the pre-charge chamber 90. The neck 104 of the sample end cap 18 defines a sample end cap face 110 which engages the face 114 of the piston 46 as shown in this figure and FIG. 1.

Figure 3:
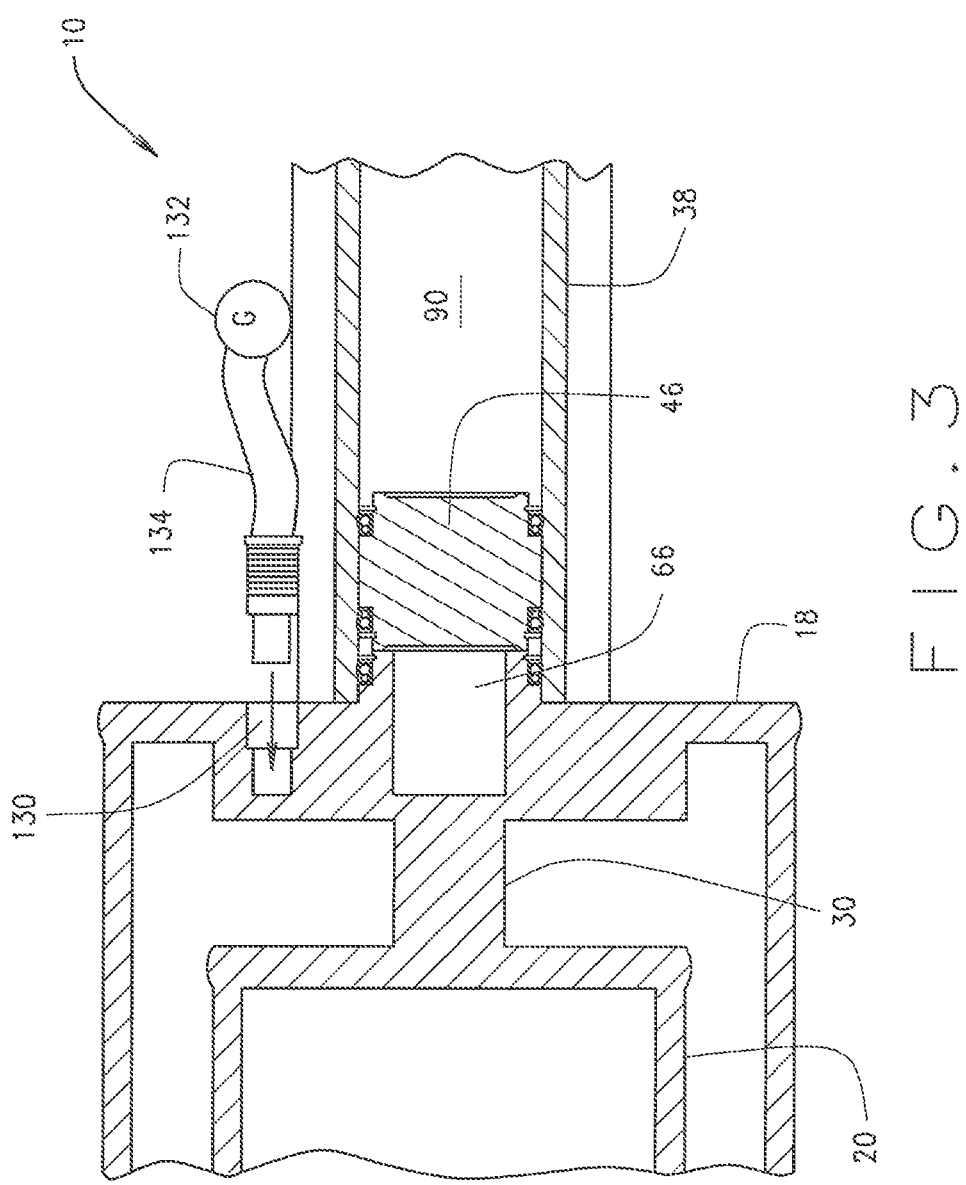
FIG. 3 is a partial section view of the Sample Apparatus of FIG. 1 rotated 90° to show a cryogenic temperature gauge.

FIG. 3 is a partial section view of the Sample Apparatus 10 of FIG. 1 rotated 90° to better show a temperature gauge 132. A blind hole port 130 is drilled in the sample end cap 18. A cryogenic gauge 132, which consists of a visual dial read-out and a flexible thermocouple housing 134 that ends in a threaded fitting sized and arranged to engage the blind hole port 130. The purpose of the cryogenic gauge is to measure the temperature of the sample end cap 18 during the pre-cool cycle, described below.

Example of Operation

In one embodiment, the transportable Liquid Phase LNG Sample Apparatus may be fabricated from 316 stainless steel, which is cryogenically compatible and capable of working with cryogenic liquids at temperatures of at least −250° F. One embodiment of the Sample Apparatus may be built with the following specifications:

The inner cryogenic vessel in the vacuum flask holds about one liter of liquid Nitrogen.

The sample cylinder is rated for about 1,000 psi.

The sample cylinder has a total capacity about 500 cc.

The LNG sample collection chamber has a capacity of about 20 cc.

The pre-charge chamber of the Sample Apparatus is pre-charged with Nitrogen gas to about 500 psi.

The Sample Apparatus weighs less than 45 pounds full.

The burping relief valve 26 opens at about 35 psi.

The frangible bursting relief 88 opens at about 1,000 psi.

The cross-sectional area of the heat exchange element is about 0.7854 square inches.

The operating cycle for the above embodiment of the present invention is as follows:

Make Ready. Using the aforementioned embodiment, the pre-charge chamber is pressurized to about 500 psi with Nitrogen gas to drive the piston into contact with the sample end cap. The piston face forms one side of the LNG sample collection chamber as shown in FIG. 1. After pressurizing the pre-charge chamber the shut off valve 80 is closed. A vacuum is drawn through the vacuum port in the vacuum chamber to about 20 inches of mercury. The vacuum is held in the vacuum chamber by the one way check valve 35. The vacuum may be drawn first or the vacuum may be drawn second after pressurizing the pre-charge chamber.

Pre-Cool Cycle. The Sample Apparatus is stood on end with the vacuum flask on top, to facilitate filling of the inner cryogenic vessel with liquid Nitrogen. (The vacuum flask is positioned opposite the earth.) The vacuum flask may also be referred to as a Dewar flask, after the inventor, Sir James Dewar.

To pre-cool at least portions of the Sample Apparatus, liquid Nitrogen, or any other cryogenic liquid, is introduced into the inner cryogenic vessel. About one liter of liquid Nitrogen is needed to fill the inner cryogenic vessel, in this embodiment of the Sample Apparatus. After the inner cryogenic vessel is full of the cryogenic fluid, a fill valve is closed and a burping check valve is attached to the vent port of the vacuum flask, sealing in the cryogenic fluid. The liquid Nitrogen is insulated by the air in the vacuum chamber of the vacuum flask. The cryogenic temperature gauge 132 is used to measure the falling temperature in the sample end cap 18 during the pre-cool cycle. When the pre-cool cycle is complete, the cryogenic temperature gauge 132 will read about −230° F. to about −260° F., and optimally about −250° F.

Filling the inner cryogenic vessel, sealing it against atmosphere and waiting for the sample apparatus to cool takes about 5 to about 10 minutes compared to about 40 to about 45 minutes for some prior art. During the pre-cool cycle, heat from the sample end cap, the sample collection chamber and the piston is dissipated through the heat exchange element to the liquid phase Nitrogen in the inner cryogenic vessel. Those skilled in the art know that if LNG is placed in an un-insulated metal container at 70° F., the LNG will immediately begin to boil off. (The term "boil off" is a phrase commonly used in this industry which means convert from liquid phase to gas phase.) Therefore, to capture a liquid phase LNG sample, it is first necessary to pre-cool the sample end cap, sample collection chamber, and piston.

Capture Cycle. After the pre-cool cycle, the Sample Apparatus will stay cold for about 30 to about 40 minutes depending on ambient temperatures, whereas some prior art devices would only stay cold for about 5 to about 10 minutes. After the "pre-cool cycle", the operators circulate liquid phase LNG through the sample end cap and the sample collection chamber for several minutes to make sure that the there is nothing but liquid phase LNG in the sample collection chamber. The LNG is circulated long enough to purge air from the sample collection chamber which typically takes from about 2 to about 3 minutes.

To capture the sample in the sample collection chamber, the outlet valve connected to the outlet port of the sample end cap is closed and an inlet valve connected to the inlet port of the sample end cap is closed. The circulation and capture of the liquid phase sample of LNG may be referred to as the "capture cycle". The pre-charge gas may be vented to atmosphere after the LNG sample has been captured in the sample collection chamber, or thereafter.

Transport. Thereafter, the Sample Apparatus is transported from the collection point to a laboratory for analysis.

Vaporizing Cycle. Vaporization of the liquid phase sample may take place at a variety of different locations. For example, vaporization may begin and end during transport from the collection point to the laboratory. In another example, vaporization may begin and be completed in the laboratory. In yet another example, vaporization may begin during transport and be completed at the laboratory. The gas phase sample is then analyzed, typically by a GC.

After the lab technicians have completed analysis of the gas phase sample, and after all liquid phase materials have converted to gas phase, the Sample Apparatus will be examined, cleaned, and reused. Although not recommended, LNG may be substituted for the liquid Nitrogen in the inner cryogenic vessel.

Figure 4:
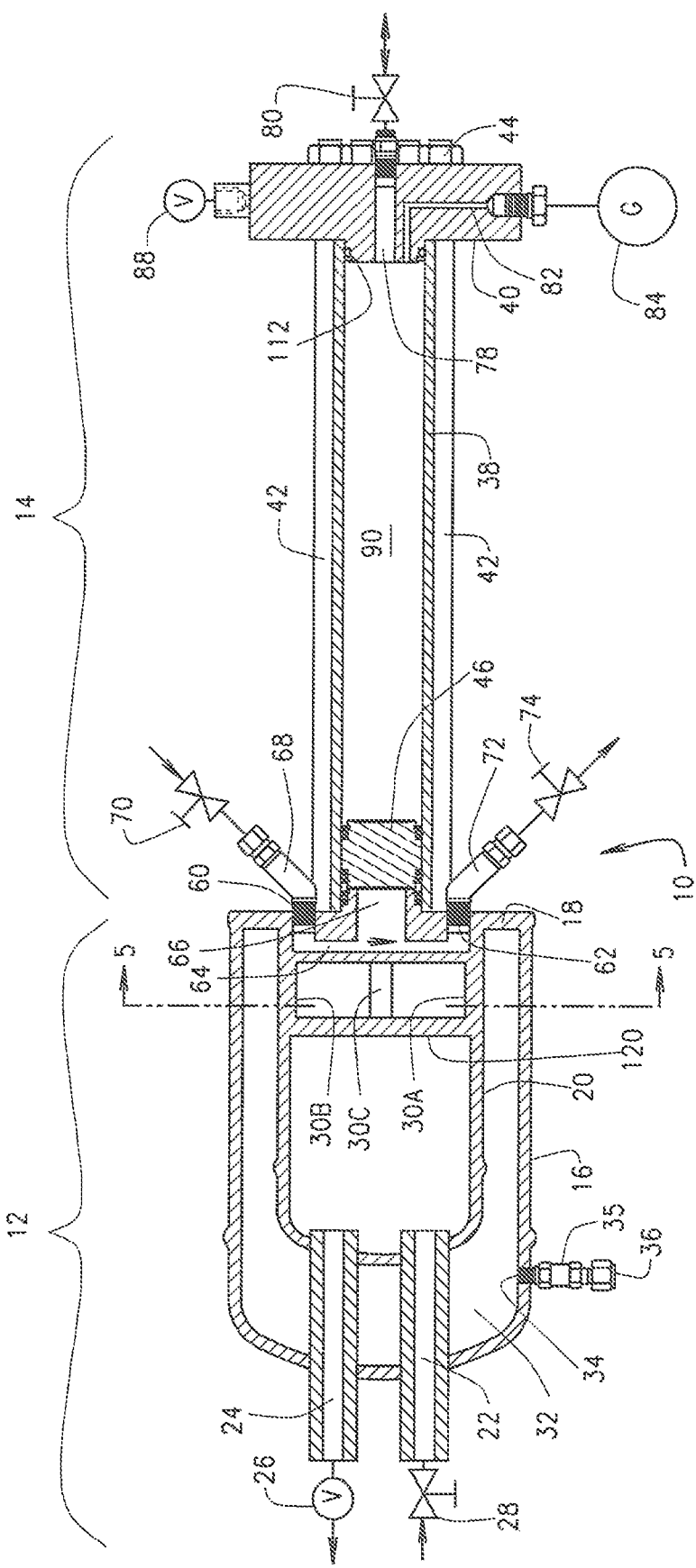
FIG. 4 is a section view of an alternative embodiment of the Sample Apparatus including the vacuum flask and sample container.

FIG. 4 is a section view of an alternative embodiment of the Sample Apparatus including the vacuum flask and sample container. This alternative embodiment uses four columnar heat exchange elements, 30 A, 30 B, 30 C, and 30 D in lieu of the single heat exchange element 30 as shown in FIG. 1. The heat exchange elements 30 A, 30 B, 30 C, and 30 D are a means for transferring heat from the sample end cap 18 to the cryogenic vessel to pre-cool the LNG sample collection chamber. Those skilled in the art will recognize that the heat exchange element and/or elements may take various physical forms, such as the single element in FIG. 1, the multiple columnar elements in FIG. 4 or other shapes such as square shaped columns, triangular shaped columns, etc. The shape and number of the heat exchange element and/or elements is not particularly important; rather, what is important is there is enough cross-sectional common area in contact with the inner cryogenic vessel and the sample end cap to rapidly transfer heat from the sample end cap and to rapidly pre-cool the sample end cap so a cryogenic sample may be taken. In the embodiment shown in FIG. 4, the combined cross-sectional area of the four heat exchange elements is 0.7854 square inches. This cross-sectional area may vary depending on the size of the Sample Apparatus.

Figure 5:
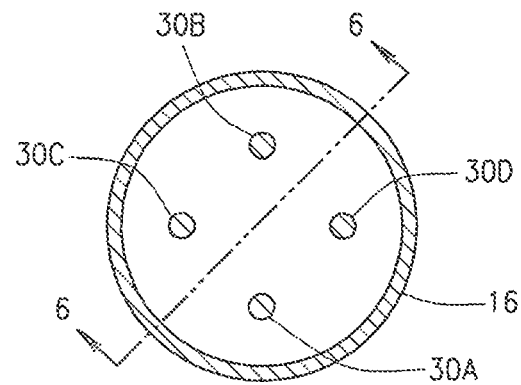
FIG. 5 is a section view along the line 5-5 of FIG. 4.
Figure 6:
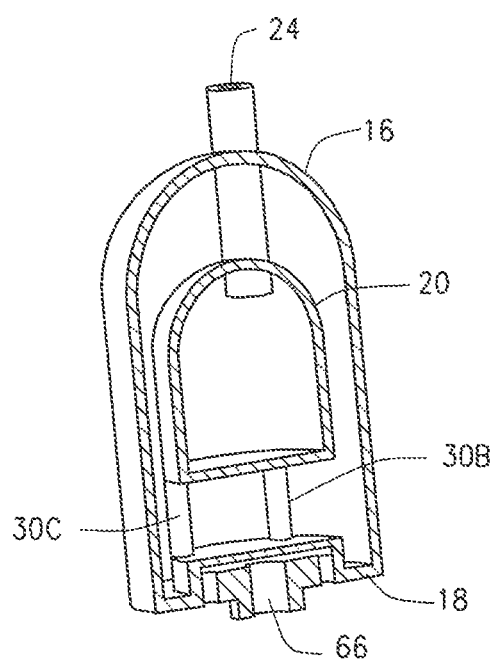
FIG. 6 is a perspective of the vacuum flask along the line 6-6 of FIG. 5.
Figure 7:
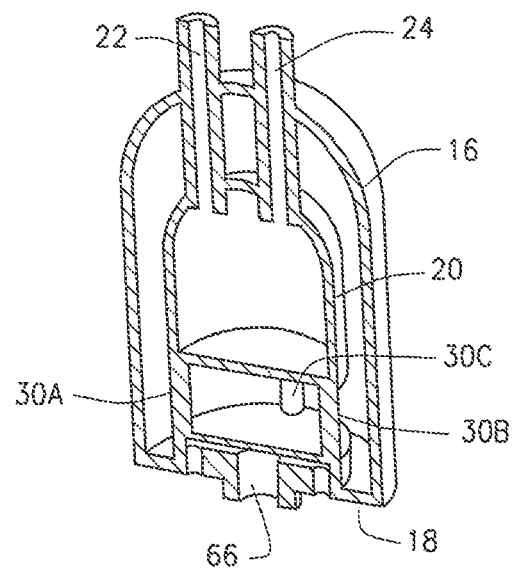
FIG. 7 is a perspective of the vacuum flask as shown in FIG. 4.

FIG. 5 is a section view along the line 5-5 of FIG. 4 showing the four columnar heat exchange elements 30 A, 30 B, 30 C and 30 D between the sample end cap 18 and the inner cryogenic vessel 20. In this view, the heat exchange elements are shown along the outer circumference of the inner cryogenic vessel, but they could also be relocated, as long as they are in contact with the inner cryogenic vessel and the sample end cap. FIGS. 6 and 7 are perspective views of the vacuum flask 16, the inner cryogenic chamber 20 and the heat exchange elements 30 A, 30 B, 30 C and 30 D.

Figure 8:
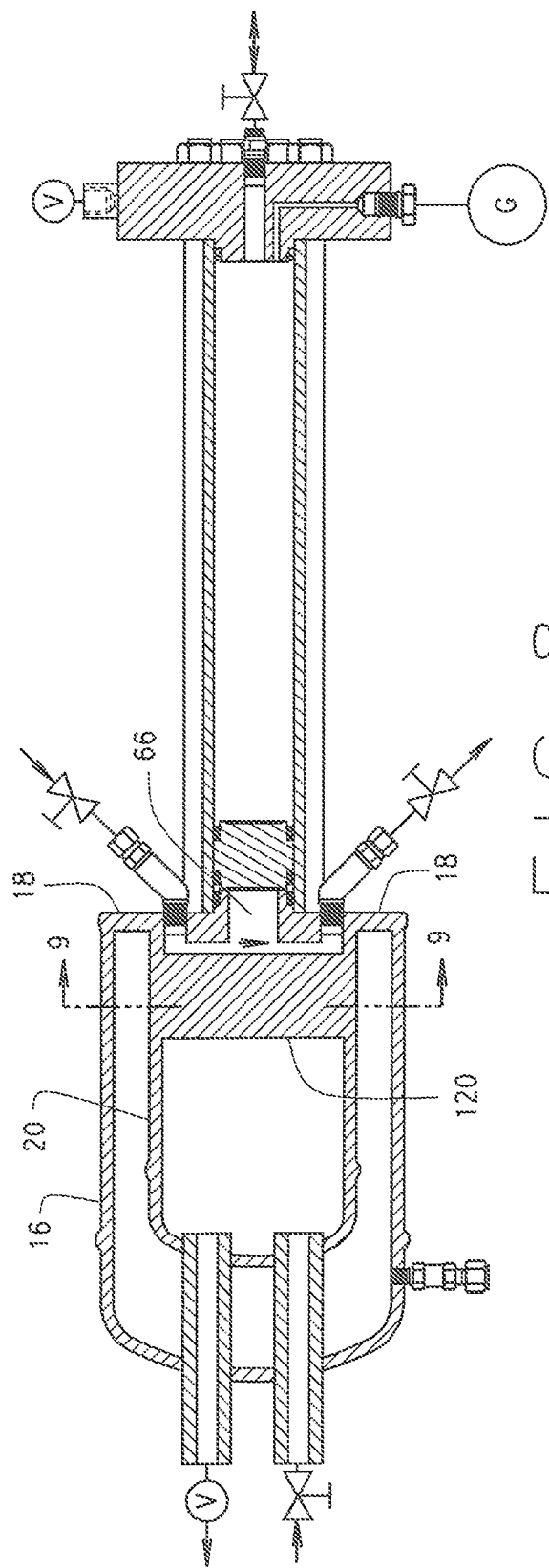
FIG. 8 is a section view of an alternative embodiment of the Sample Apparatus including the vacuum flask and sample container.
Figure 9:
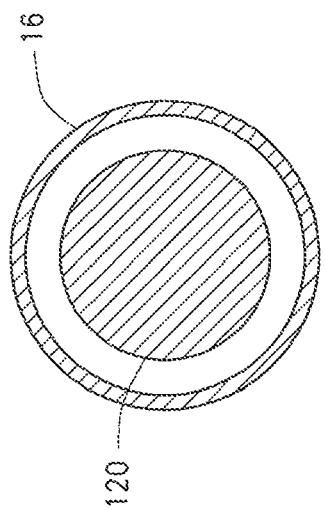
FIG. 9 is a section view along the line 9-9 of FIG. 8.

FIG. 8 is a section view of an alternative embodiment of the Sample Apparatus including the vacuum flask and sample container. In this alternative embodiment, the base 120 of the inner cryogenic vessel 20 is flush with the sample end cap 18. This allows the base 120 to act as a means for transferring heat from the sample end cap to the inner cryogenic vessel to pre-cool the sample end cap and the LNG sample collection chamber. FIG. 9 is a section view along the line 9-9 of FIG. 8.

The invention claimed is:

1. A sample apparatus for capture of a liquid phase sample of liquefied natural gas (LNG) comprising:
    a LNG sample container having;
    a hollow cylinder captured between and sealed against a sample end cap and a pre-charge end cap;
    a piston positioned in and sealed against the hollow cylinder, the piston selectively movable toward and away from the sample end cap and pre-charge end cap;
    the sample end cap defining a sample inlet port, portions of a sample collection chamber and a sample outlet port, the sample inlet port, the sample collection chamber and the sample outlet port all being in fluid communication with one another;
    a vacuum flask having;
    an outer shell, connected to the sample end cap;
    an inner cryogenic vessel having a base;
    a vacuum chamber formed between the outer shell and the inner cryogenic vessel to insulate the inner cryogenic vessel;
    a fill port passing through the outer shell and in fluid communication with the inner cryogenic vessel, a vent port from the inner cryogenic vessel passing through the outer shell and a vacuum port in the outer shell in fluid communication with the vacuum chamber; and
    means for transferring heat from the sample end cap to the inner cryogenic vessel.

2. The apparatus of claim 1 wherein the means for transferring heat is a heat exchange element in contact with a portion of the cryogenic vessel and a portion of the sample end cap to pre-cool the sample end cap.

3. The apparatus of claim 1 wherein the means for transferring heat is a plurality of heat exchange elements in contact with a portion of the cryogenic vessel and a portion of the sample end cap to pre-cool the sample end cap.

4. The apparatus of claim 1 wherein the means for transferring heat is the base of the cryogenic vessel.

5. The apparatus of claim 1 wherein the LNG sample container further includes:
    a pre-charge chamber defined by the pre-charge end cap, a portion of the hollow cylinder and the piston; and
    a pre-charge port formed in the pre-charge end cap to allow a pre-charge gas to be placed in the pre-charge chamber of the LNG sample container driving the piston into contact with the sample end cap and forming a side of the LNG sample collection chamber.

6. The apparatus of claim 5 further including a temperature gauge in the sample end cap.

7. The apparatus of claim 6 further including a shut off valve in the cryogenic fill port and a burping relief in the vent port of the cryogenic vessel.

8. The apparatus of claim 7 wherein the burping relief valve is set to open at about 35 psi.

9. The apparatus of claim 8 further including a frangible bursting relief valve in fluid communication with the pre-charge chamber to protect against overpressure in the pre-charge chamber.

10. A sample apparatus for capture of a liquid phase sample of liquefied natural gas (LNG) comprising:
    a LNG sample container having;
    a hollow cylinder captured between and sealed against a sample end cap and a pre-charge end cap;
    a piston positioned in and sealed against the hollow cylinder, the piston selectively movable toward and away from the sample end cap and pre-charge end cap;
    the sample end cap defining a sample inlet port, portions of a sample collection chamber and a sample outlet port, the sample inlet port, the sample collection chamber and the sample outlet port all being in fluid communication with one another;
    a vacuum flask having;
    an outer shell, connected to the sample end cap;
    an inner cryogenic vessel having a base;
    a vacuum chamber formed between the outer shell and the inner cryogenic vessel to insulate the inner cryogenic vessel;
    a fill port passing through the outer shell and in fluid communication with the inner cryogenic vessel, a vent port from the inner cryogenic vessel passing through the outer shell and a vacuum port in the outer shell in fluid communication with the vacuum chamber; and the base of the inner cryogenic vessel is flush against the sample end cap to transfer heat from the sample end cap to the inner cryogenic vessel.

* * * * *